(12) United States Patent
Berner

(10) Patent No.: US 11,116,608 B2
(45) Date of Patent: Sep. 14, 2021

(54) PROCESS FOR THE PREPARATION OF A TOPOGRAPHY FOR IMPROVED BLOOD COAGULATION AND/OR CELL ATTACHMENT ON A BODY MADE OF TITANIUM OR A TITANIUM ALLOY

(71) Applicant: STRAUMANN HOLDING AG, Basel (CH)

(72) Inventor: Simon Berner, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 342 days.

(21) Appl. No.: 15/576,346

(22) PCT Filed: May 26, 2016

(86) PCT No.: PCT/EP2016/061932
§ 371 (c)(1),
(2) Date: Nov. 22, 2017

(87) PCT Pub. No.: WO2016/189097
PCT Pub. Date: Dec. 1, 2016

(65) Prior Publication Data
US 2018/0147029 A1  May 31, 2018

(30) Foreign Application Priority Data
May 26, 2015 (GB) .................................. 1508958

(51) Int. Cl.
*A61C 8/00* (2006.01)
*A61L 27/06* (2006.01)
*A61L 27/50* (2006.01)
*A61C 8/02* (2006.01)

(52) U.S. Cl.
CPC .......... *A61C 8/0015* (2013.01); *A61C 8/0006* (2013.01); *A61L 27/06* (2013.01);
(Continued)

(58) Field of Classification Search
CPC .......... A61C 8/00; A61C 7/00; A61C 8/0015; A61F 2/30; B24C 11/00; H01L 23/00
See application file for complete search history.

(56) References Cited

U.S. PATENT DOCUMENTS 5,573,401 A * 11/1996 Davidson ................. A61K 6/84
433/201.1
5,603,338 A * 2/1997 Beaty ....................... A61C 8/00
128/898

(Continued)

FOREIGN PATENT DOCUMENTS

CN 1985774 A 6/2007
CN 103654979 A * 11/2013 ............... A61C 8/00

(Continued)

OTHER PUBLICATIONS

Aug. 29, 2016 Search Report issued in International Patent Application No. PCT/EP2016/061932.

(Continued)

*Primary Examiner* — Dah-Wei D. Yuan
*Assistant Examiner* — Andrew J Bowman
(74) *Attorney, Agent, or Firm* — Oliff PLC

(57) ABSTRACT

A process for the preparation of a topography for improved blood coagulation and/or cell attachment on a body made of titanium or a titanium alloy. The process includes the subsequent steps of: a) etching at least a portion of the surface of the body with a first etching solution including a mineral acid, and b) etching the surface etched under a) with a second etching solution different than the first etching solution, the second etching solution including hydrofluoric acid.

14 Claims, 10 Drawing Sheets

(52) U.S. Cl.
CPC ........... *A61L 27/50* (2013.01); *A61L 2400/18* (2013.01); *A61L 2430/12* (2013.01)

(56) References Cited

U.S. PATENT DOCUMENTS

| | | | | |
|---|---|---|---|---|
| 2004/0265780 | A1* | 12/2004 | Robb | C23F 1/26 |
| | | | | 433/173 |
| 2008/0113316 | A1* | 5/2008 | Menke | A61C 8/0018 |
| | | | | 433/174 |
| 2009/0088858 | A1* | 4/2009 | Zinger | C23G 1/106 |
| | | | | 623/18.11 |
| 2009/0283701 | A1* | 11/2009 | Ogawa | B23K 26/355 |
| | | | | 250/492.1 |
| 2014/0277483 | A1* | 9/2014 | Ullrich, Jr. | A61F 2/28 |
| | | | | 623/17.16 |
| 2015/0221605 | A1* | 8/2015 | Atanasova | H01L 24/11 |
| | | | | 257/737 |

FOREIGN PATENT DOCUMENTS

| | | | | | |
|---|---|---|---|---|---|
| CN | 103654979 | A | * | 3/2014 | ............ A61C 8/00 |
| CN | 103654979 | A | | 3/2014 | |
| CN | 1985774 | | * | 6/2017 | ............ A61C 13/08 |
| EP | 1477141 | | * | 11/2004 | ............ A61F 2/30 |
| EP | 1477141 | A1 | | 11/2004 | |
| JP | H03-146679 | A | | 6/1991 | |
| WO | 2006/091582 | A2 | | 8/2006 | |
| WO | WO2006/091582 | | * | 8/2006 | ............ B05D 3/02 |
| WO | 2013/056844 | A1 | | 4/2013 | |

OTHER PUBLICATIONS

Aug. 29, 2016 Written Opinion issued in International Patent Application No. PCT/EP2016/061932.

Gittens et al., "The Effects of Combined Micron-/Submicron-Scale Surface Roughness and Nanoscale Features on Cell Proliferation and Differentiation", Biomaterials, vol. 32, pp. 1-21, 2011.

Nov. 28, 2017 International Preliminary Report on Patentability issued in International Patent Application No. PCT/EP2016/061932.

Saulacic, N., et al. "Bone apposition to a titanium-zirconium alloy implant, as compared to two other titanium-containing implants." European Cells and Materials. vol. 23, 2012, pp. 273-288.

\* cited by examiner

PROCESS FOR THE PREPARATION OF A TOPOGRAPHY FOR IMPROVED BLOOD COAGULATION AND/OR CELL ATTACHMENT ON A BODY MADE OF TITANIUM OR A TITANIUM ALLOY

TECHNICAL FIELD

The present invention relates to a process for the preparation of a topography for improved blood coagulation and/or cell attachment on a body made of titanium or a titanium alloy, to a body obtainable by this process as well as to the use of the body for a dental implant or a dental implant abutment.

BACKGROUND

Implants, such as dental implants, are well known in the art. They generally consist of a material, which is biocompatible and which additionally has favourable mechanical properties. Currently used dental implants are often made of titanium or a titanium alloy, which apart from being biocompatible exhibit outstanding mechanical strength.

The acceptance of the human body towards an implant is determined by the implant surface. When detected as a foreign object and rejected by the immune system, the implant may cause inflammation, which not only causes pain to the patient but often also leads to the necessity of a second surgery to remove or replace the implant.

In order to avoid rejection of the implant by the human body, the implant surface must be engineered in a manner that cells attach to it and that natural body tissue, specifically bone tissue or soft tissue, start growing around the implant.

In the case of a dental implant, for example, it is required that a direct structural and functional connection between living jaw bone and the implant surface is achieved shortly after implantation. This is referred to in the art as "osteointegration" (or "osseointegration"): a good osteointegration means that the implant safely ossifies within a short healing time so that a permanent bond between implant and bone is obtained.

Besides the importance of the osteointegrative properties, there is increasing evidence that also a good interaction between the dental implant and the surrounding supracrestal connective tissue (in the following referred to as the "soft tissue") is crucial for a successful implantation. This is supported by the view that the soft tissue plays a fundamental role in establishing an effective seal between the oral environment and the endosseous part of a dental implant and, thus, also a barrier for bacteria to adhere on the soft tissue contact surface and the bone tissue contact surface of the implant.

The attachment of cells of the surrounding soft or bone tissue is governed by proteins which adhere, i.e. adsorb, to the surface once the implant gets in contact with blood. It is assumed that the proteins adsorbed on the implant surface influence the behaviour, e.g. the differentiation, of the cells of the respective tissue.

In order to achieve a fast and strong interaction between the dental implant and the respective tissue, adherence of these proteins on the surface is thus of paramount importance.

One important factor that influences protein adherence is the hydrophilicity of the surface.

Recently, it has been found that also the presence of specific nanostructures may play an important role in the adherence of proteins.

Specifically, WO2013/056844 describes a process for providing structures for an improved protein adherence on the surface of a body, specifically an implant. The process comprises the step of storing an acid-etched basic body in an aqueous solution, by which nanostructures are formed on the surface of the basic body. According to WO2013/056844, the formation of nanostructures thereby occurs gradually in that they "grow" or "build up" over time.

Further, R. A. Gittens et al. (Biomaterials 32 (2011) 3395-3403) report on studies focussing on the hierarchical combination of both micro- and nanoscale roughness to promote osseointegration on clinically-relevant surfaces.

Notwithstanding the good results achieved according to the process of WO2013/056844, there is an ongoing need for providing a body which after implantation establishes a fast and strong interaction with the surrounding tissue.

SUMMARY

In consideration of this, the object to be solved by the present invention is to provide a process for preparing a topography on a body made of titanium or a titanium alloy in a manner to allow for an improved interaction with the surrounding tissue. In particular, a simple and reproducible process for modifying the body's surface shall be provided which allows for a relatively selective adherence of at least one blood protein mediating blood coagulation and/or cell attachment and, thus, tissue interaction with the body.

The object of the present invention is solved by the process according to claim 1. Preferred embodiments of the invention are defined in the dependent claims.

According to claim 1, the process of the present invention is directed to the preparation of a topography for improved blood coagulation and/or cell attachment on a body made of titanium or a titanium alloy, i.e. the most common material used for dental implants or dental implant abutments.

The process comprises the subsequent steps of
a) etching at least a portion of the surface with a first etching solution comprising a mineral acid, and
b) etching the surface etched under a) with a second etching solution different than the first etching solution, said second etching solution comprising hydrofluoric acid (HF).

DETAILED DESCRIPTION

Figure 1:
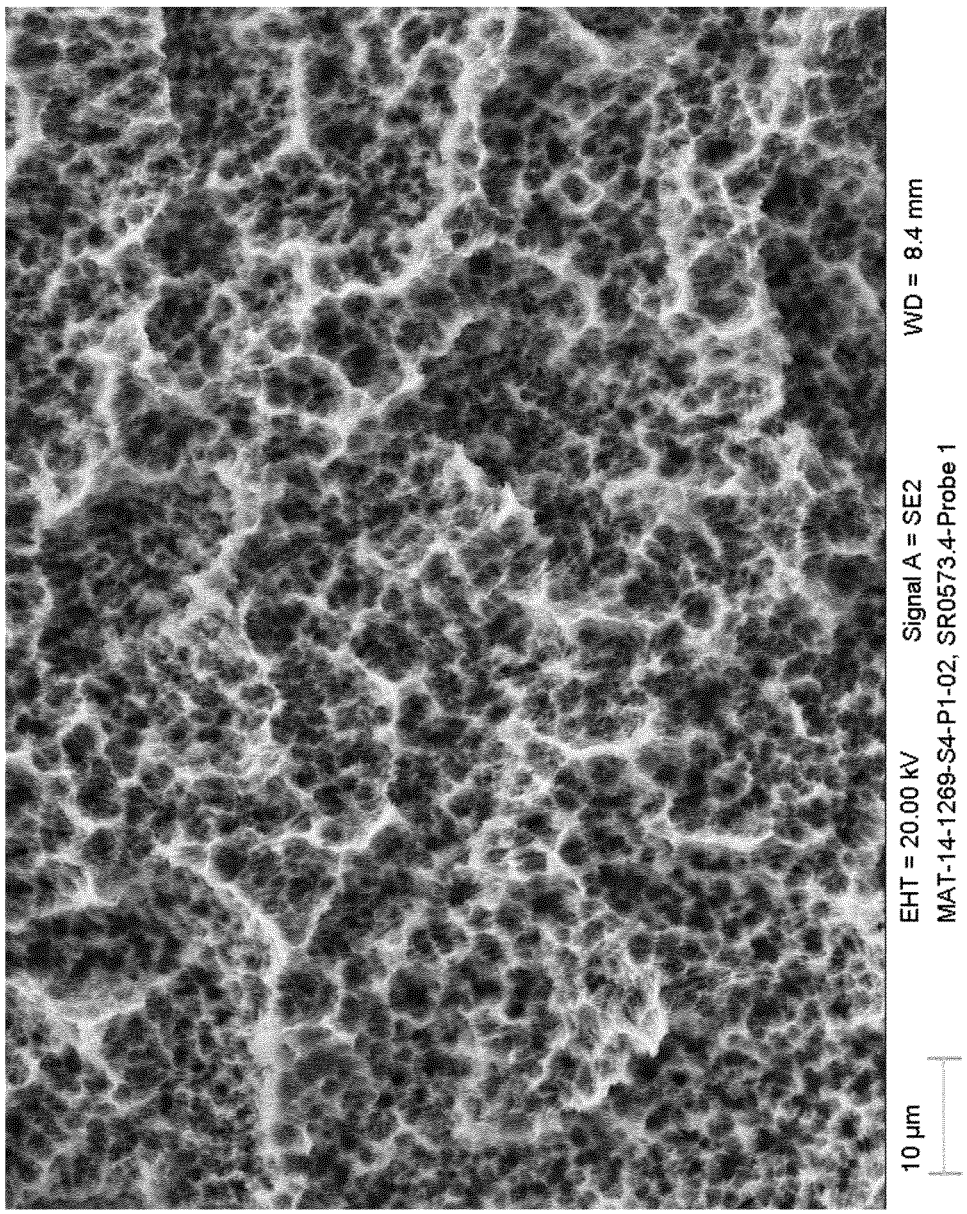
FIG. 1 shows a Scanning Electron Microscopy (SEM) image of the surface of sample RXD SLA HF in a magnification of about 1,000×.

It has surprisingly been found that by the combined etching according to the present invention, a surface is achieved which allows for a fast blood coagulation and, hence, formation of the fibrin network and/or a strong attachment of the cells of the surrounding tissue. In particular, an improved osteointegration of the body is achieved, as will be shown in detail by way of the specific working examples described below.

It has further been found that an improved tissue interaction, specifically osteointegration, can be achieved, even in the case when the surface of the body is relatively hydrophobic. This finding is most surprising given the established doctrine that a hydrophilic surface is an important requirement for achieving a good osteointegration.

Without wanting to be bound by the theory, it is assumed that the improved blood coagulation and/or cell attachment is due to the body's specific topography obtained by the process of the present invention, according to the following mechanism:

When a body is implanted into tissue, particularly into bone tissue, it is first contacted by water molecules from the surrounding blood. In a next step, ions and proteins will accumulate and adhere on the implant's surface, but without actually penetrating the material. As mentioned above, this "protein adherence" or "protein adsorption" is assumed to be decisive for later cell responses.

By the specific topography obtainable by the present invention, "protein retention structures" are provided on the body's surface, i.e. structures which allow an improved adherence of specific proteins.

As will be shown by way of the attached working examples, the topography obtained allows for a relatively selective adherence of fibrinogen, to which an important role in the blood coagulation and, hence, the formation of the fibrin network is attributed. In this context, the working examples also show that relatively thick fibrin networks are formed on a body according to the present invention in comparison to the comparative examples.

The term "etching" as used in the context of the present invention is to be understood broadly and encompasses any formation or alteration of the topography of the body by means of the etching solution dissolving and therefore removing material from the surface of the body. Etching, thus, relates to a subtractive surface treatment, which is in contrast to any additive surface treatment, as it is e.g. the case for an anodization treatment. According to a specific embodiment, the term "etching" does not relate to a mere removal of the native oxide layer of the body, since this native oxide removal does not go along with a formation or alteration of the topography. An etching within the meaning of this embodiment is likewise in contrast to a "pickling" treatment, which is used to remove surface impurities and aims at a preferentially homogeneous material removal.

Specifically, by etching the surface according to step a) a microscopic topographical formation is formed, and by etching the surface according to step b) a sub-microscopic topographical formation is formed in the microscopic topographical formation. Thus, a formation of different topographical scale is formed in step b) than in step a), leading to a hierarchical topography.

As will be further discussed in detail below, subtractive process step a) preferably corresponds to the acid etching according to the well-known SLA® treatment. Specifically, step a), thus, relates to a pre-treatment comprising a mechanical subtractive treatment, more particularly a sandblasting treatment, prior to the etching.

Like step a), step b) is also a subtractive process step, meaning that by this step, material is removed from the body. The term that the sub-microscopic topographical formation is "formed in the microscopic topographical formation" is therefore to be understood as "formed by further removing material form the intermediate body obtained after step a) having the microscopic topographical formation".

The sub-microscopic topographical formation obtained by the process of the present invention is thus made of material initially contained in the body and remaining on the body's surface after step a) and step b). The manner in which the sub-microscopic topographical formation is formed is thus in all respects different to the formation of nanostructures described in WO2013/056844, which relates to the growing or building up of structures over time and, therefore, to an additive process.

Due to the process step b) being subtractive, the material composition of the sub-microscopic topographical formation essentially corresponds to the material composition of the body's surface before treatment as well as to the material composition of the microscopic topographical formation present after process step a). Since the body is made of titanium or a titanium alloy having a surface on which a respective oxide layer is spontaneously formed, the microscopic topographical formation with the sub-microscopic topographical formation formed thereon is likewise made of titanium or a titanium alloy, respectively, with an oxide layer formed thereon.

Since both step a) and step b) are etching steps, the process of the present invention can be regarded a "dual etching" process. It is, thus, in any respect different from a process which comprises merely one single etching step, i.e. one single subtractive surface treatment step. In particular, it is in clear contrast to a two-step treatment, in which a single etching step is followed by an additive surface treatment step, such as an anodization step, for chemically modifying the surface and/or for structuring its topography.

According to a preferred embodiment of the present invention, the microscopic topographical formation is defined by at least one of the following surface parameters:

i) $S_a$ being the arithmetic mean deviation of the surface in three dimensions and being in the range from 0.1 µm to 2.0 µm, preferably being in a range from 0.4 µm to 1.8 µm, more preferably from 0.8 µm to 1.7 µm, and most preferably from 0.9 µm to 1.5 µm;

ii) $S_t$ being the maximum peak to valley height of the profile in three dimensions and being in the range from 1.0 µm to 20.0 µm, preferably being in a range from 3.0 µm to 18.0 µm, more preferably from 4.5 µm to 13.0 µm, and most preferably from 6.0 µm to 12.0 µm; and/or iii) $S_{sk}$ being the skewness of the profile in three dimensions and being in the range from −0.6 to 1.0, preferably from −0.4 to 0.6, more preferably from −0.3 to 0.5.

The surface parameters are known to the skilled person and are analogue parameters for three dimensions to the parameters $R_a$, $R_t$ and $R_{sk}$, respectively, defined in EN ISO 4287 for two dimensions. Specifically, the above values relate to the values as e.g. obtainable by the WinSAM software (SAM (Surface Analysis Method) for Windows) known to the skilled person.

The above values for $S_a$, $S_t$ and $S_{sk}$ relate in particular to a bone contacting surface of the body, i.e. a surface area located such on the body, specifically the implant, to come into contact with bone tissue after implantation. For a soft tissue contacting surface of the body, the preferred values are smaller. Specifically, $S_a$ is preferably in the range from 0.05 µm to 0.5 µm, more preferably from 0.05 µm to 0.3 µm for a soft tissue contacting surface.

As mentioned, the microscopic topographical formation defined above is typically obtained by step a) further comprising a sand-blasting treatment prior to the etching.

Regarding the microscopic topographical formation, the surface parameters are preferably in the range of "SLA®" or "SLActive®" surfaces, given the above mentioned preferred embodiment in which the etching according to a) is performed according to the SLA® or SLActive® protocol.

Both the "SLA®" and "SLActive®" treatment are well-known in the respective field and relate to a breakthrough technology in view of the preparation of osteophilic implants. Specifically, "SLA®" involves sandblasting the implant's surface followed by treating it with an etching solution comprising a first mineral acid, whereas "SLActive®" further comprises conditioning the "SLA" surface either in nitrogen or in an isotonic saline solution, thereby maintaining the high hydrophilicity of the "SLA®" surface which would otherwise be lost during storage due to interaction with the atmosphere.

According to a preferred embodiment of the present invention, the first etching solution, thus, comprises or essentially consists of a mixture of HCl and $H_2SO_4$. More particularly, a mixture of HCl and $H_2SO_4$ at a temperature higher than 80° C. is used for step a). Alternatively, any other solution of at least one mineral acid can be used for process step a), in particular a solution comprising at least one mineral acid selected from the group consisting of HCl, $H_2SO_4$, $H_3PO_4$ and mixtures thereof. If HF is contained in the first etching solution, the concentration of HF is lower than the HF concentration of the second etching solution. According to a particularly preferred embodiment, the first etching solution is at least approximately devoid of HF. In this regard, the present invention is in even clearer distinction from the technology described in EP 1 477 141, according to which HF is used for removing the native oxide in a first step before etching the surface in a second step.

It is further preferred that prior to step a) a macroscopic topographical formation is provided to the surface, more preferably by sand-blasting. For example, corundum having a particle size from 250-500 µm can be used as blasting material. In this embodiment, also the sand-blasting step of the SLA® technology is applied to the process of the present invention.

According to a specifically preferred embodiment, the present invention, thus, involves the same steps as according to the SLA® protocol, but further comprising step b) after the SLA® etching step.

Preferably, the process is carried out in a manner that by the sub-microscopic topographical formation formed in step b), at least one surface parameter defining the microscopic topographical formation formed in step a) and being selected from the group consisting of $S_a$, $S_t$ and $S_{sk}$ is changed by 50% at most, preferably by 20% at most, more preferably by 10% at most and most preferably is kept essentially unchanged.

Thus, the well-established macroscopic and microscopic topographical formation according to the SLA® technology is not altered or only altered to a negligible degree by process step b). This will be further illustrated by the attached figures showing an almost identical picture at a magnification focussing on the macroscopic and microscopic topographical formation of the surface, but showing a completely different picture of the surface at a magnification focussing on the sub-microscopic topographical formation.

Specifically, the sub-microscopic topographical formation achievable by the present invention comprises or essentially consists of sub-microscopic structures which extend in at least two dimensions to 1000 nm at the most. Preferably, the sub-microscopic structures extend in at least two dimensions from 20 nm to 1000 nm, preferably from 30 nm to 500 nm, more preferably from 40 nm to 300 nm, even more preferably from 50 nm to 250 nm, and most preferably from 100 nm to 200 nm.

Depending on the specific material of the body and on the process parameters, different sub-microscopic structures can be obtained. Specifically, the sub-microscopic structures have a shape with at least one straight-line edge, and more specifically are sharp-edged and/or jagged, as will also be illustrated by way of the attached figures. Alternatively or additionally, the sub-microscopic structures can be arranged in a stepped or cascaded manner with respect to each other. More specifically, the sub-microscopic structures can be in the form of sharp-edged cliffs or columns with crevices formed between them.

Preferably, the concentration of hydrofluoric acid in the second etching solution is in the range from 0.01 vol.-% to 4 vol.-%, preferably from 0.05 vol.-% to 2 vol.-%, more preferably from 0.1 vol.-% to 1 vol.-%. Most preferably, the concentration of hydrofluoric acid in the second etching solution is in the range from 0.2 vol.-% to 0.5 vol.-%.

According to a further preferred embodiment, the etching under step b) is carried out for a duration in the range from 0.1 minute to 30 minutes, preferably from 0.5 minute to 20 minutes, more preferably from 0.5 minute to 10 minutes, most preferably from 1 minute to 5 minutes.

By keeping the concentration of hydrofluoric acid and the duration of treatment according to step b) within the preferred ranges given above, the desired sub-microscopic topographical formation can be achieved while leaving the features of both the macroscopic and the microscopic topographical formation intact. In particular, at least one of the surface parameters $S_a$, $S_t$ and $S_{sk}$ defining the microscopic topographical formation is kept essentially unchanged, which is preferable as mentioned above.

The relative short duration of etching further emphasizes the difference of the process of the present invention to the growing of nanostructures referred to in WO2013/056844, which extends over a much longer period of time.

It is further preferred that the etching in step b) is carried out at a temperature in the range from 10° C. to 90° C., preferably from 10° C. to 60° C., more preferably from 15° C. to 40° C., even more preferably from 15° C. to 30° C., and most preferably at room temperature (20° C.)

According to a further preferred embodiment, the body is made of a titanium-zirconium alloy, since for this material a surface topography of particular relevance can be achieved by the process of the present invention. More preferably, the body is made of a bimetallic titanium-zirconium alloy comprising 13-17% zirconium. A particularly preferred titanium-zirconium alloy is available under the tradename Roxolid® (Institut Straumann AG, Switzerland), the properties of which being well-known to the person skilled in the art. Depending on the aim to be achieved, the body can also be made of titanium, since it has been found that also for a body made of titanium, in particular a titanium implant, a topography for improved blood coagulation and/or cell attachment can be achieved by the process of the present invention.

As pointed out above, the process of the present invention is in particular directed to a dental implant or a dental implant abutment, in order to provide it with a surface that allows for a strong interaction with the surrounding tissue. According to a preferred embodiment, the body is a dental implant or a dental implant abutment and the topography is provided on at least a portion of the surface of the body that in use is intended to be in contact with bone tissue or soft tissue, respectively.

As also mentioned above and as will be shown in more detail by way of the working examples, improved osteointegration can be achieved by the topography provided according to the present invention, even in the case when the surface is relatively hydrophobic. Thus, the surface provides good osteointegrative properties also after storage of the dental implant in air and there is, therefore, no necessity for storing the dental implant in a protective environment. Ultimately, this allows for a very simple packaging of the dental implant.

The term "hydrophobic" or "hydrophobicity" is used as a contrary to the term "hydrophilic" or "hydrophilicity", which—as used in the context of the present invention—refers to a contact angle of the surface of less than 90°, more preferably less than 30°, most preferably less than 10°, when contacted with water.

According to a specific embodiment of the present invention, the surface of the body is hydrophobic. In the context of the present invention, the term "hydrophobic" or "hydrophobicity" specifically relates to a contact angle of the surface higher than 90°, when contacted with water. As mentioned, the specific topography achievable by the present invention allows outstanding osteointegrative properties to be obtained even in the case of relatively high contact angles. Thus, very simple packaging and storage means for the implant can be chosen, still arriving at outstanding osteointegrative properties even after a prolonged storage period.

According to a further specific embodiment, the surface of the body is hydrophilic with contact angles less than 90° C., more specifically superhydrophilic with contact angles less than 30°, most specifically less than 10°, when contacted with water. The surface being hydrophilic or superhydrophilic leads to instant wetting of the implant with blood, and thus to a fast contact of water molecules and ions contained therein, followed by the accumulation and adherence of blood coagulation- and/or cell attachment-mediating proteins on the surface. By this, even further improved interaction of the surface with the surrounding tissue can be obtained.

Apart from the process described above, the present invention also relates to a body obtainable by the process.

Specifically, the invention relates to a body, the surface of which being defined by a microscopic topographical formation and by a sub-microscopic topographical formation formed in the microscopic topographical formation.

As mentioned above, the microscopic topographical formation is defined by at least one of the following surface parameters:

i) $S_a$ being the arithmetic mean deviation of the surface in three dimensions and being in the range from 0.1 µm to 2.0 µm, preferably being in a range from 0.4 µm to 1.8 µm, more preferably from 0.8 µm to 1.7 µm, and most preferably from 0.9 µm to 1.5 µm;

ii) $S_t$ being the maximum peak to valley height of the profile in three dimensions and being in the range from 1.0 µm to 20.0 µm, preferably being in a range from 3.0 µm to 18.0 µm, more preferably from 4.5 µm to 13.0 µm, and most preferably from 6.0 µm to 12.0 µm; and/or iii) $S_{sk}$ being the skewness of the profile in three dimensions and being in the range from −0.6 to 1.0, preferably from −0.4 to 0.6, more preferably from −0.3 to 0.5.

Specifically, the above values relate to the values as e.g. obtainable by the WinSAM software (SAM (Surface Analysis Method) for Windows) known to the skilled person, as mentioned above.

As also mentioned, the sub-microscopic topographical formation comprises or consists of sub-microscopic structures which extend in at least two dimensions to 1000 nm at most.

Still further and in accordance with the process described above, at least some of the sub-microscopic structures have a shape with at least one straight-line edge, and particularly are sharp-edged and/or jagged. Alternatively or additionally, the sub-microscopic structures can be arranged in a stepped or cascaded manner with respect to each other.

It is understood that all features which are described above as preferred features of the process also are preferred features of the body of the present invention and vice versa.

According to a still further aspect, the present invention also relates to the use of the body according to any of the preceding claims for a dental implant or a dental implant abutment. In this regard, the body can be used as the dental implant or the dental implant abutment or as a part of the dental implant or dental implant abutment. It is understood that when the body is used as a part of the dental implant or dental implant abutment, at least a portion of the remaining part can be made of a material other than titanium or titanium alloy, respectively.

If the body is used as a dental implant abutment, the values for $S_a$, $S_t$ and $S_{sk}$ are preferably lower than the ones mentioned above, which in particular relate to a bone contacting surface of the body. Specifically, $S_a$ is in the case of the body being a dental implant abutment preferably in the range from 0.05 µm to 0.5 µm, and more preferably from 0.05 µm to 0.3 µm. This allows a particularly strong interaction of the dental implant abutment and the surrounding soft tissue to be obtained.

EXAMPLES

1. Examples Relating to In Vitro-Analysis 1.1. Materials and Methods
Material
Discs, 5 mm in diameter and 1 mm in thickness, were prepared from a bimetallic TiZr alloy rod (Roxolid (RXD); 13-17% Zr).
"SLA" Treatment
First, the samples have been treated according to the protocol for preparing "SLA®" samples. Specifically, the samples have been sand-blasted using corundum with large grits (particle size 250-500 µm), followed by etching the sand-blasted surface in a boiling mixture of HCl and $H_2SO_4$.
Samples "RXD SLA HF" and "RXD SLActive HF"
A first portion of the samples achieved by the SLA® treatment (involving step a) of the process of the present invention) has then been treated in an aqueous solution comprising 0.2% hydrofluoric acid (volumes for 100 ml: 0.5 ml 40% HF, 99.5 ml H$_2$O) for 2 minutes (corresponding to step b) of the process) at room temperature.

The samples have then been rinsed in ultrapure water by placing a Teflon beaker containing the samples in 400 ml ultrapure water and subjecting the samples to ultra-sonication three times (1 minute each in approximately 20 ml ultrapure water). The samples have then been blown dry in a stream of argon and stored dry in aluminium foil.

Thereby, samples "RXD SLA HF" according to the present invention have been achieved.

Further, samples "RXD SLActive HF" have been prepared, which will be discussed in the context of the assessment of the fibrin network formation. Specifically, these samples have been prepared in analogy to the "RXD SLA HF" described above, but with the difference that instead of storing the dried samples in air, storage was carried out in 0.9% NaCl solution (pH of approximately 5) in a vial used for the commercially available SLActive® implants.

Samples "RXD SLActive"

For comparative purposes, a second portion of the samples achieved by the SLA® treatment has been directly immersed and stored in 0.9% NaCl solution, according to the SLActive® protocol, whereby comparative samples "RXD SLActive" have been achieved.

Storage and Sterilization

All samples were stored for a minimum duration of 2 months.

Both the RXD SLA HF and the RXD SLActive samples were γ(gamma)-sterilized (25-42 kGy) before analysing their surface according to the evaluation methods described in the following. Comparison experiments conducted on discs before and after sterilization showed no indication of an influence of the γ(gamma)-sterilization on the results obtained by the following evaluation methods.

1.2. Evaluation Methods 1.2.1. Contact Angle Measurements

Contact angle measurements were performed in order to determine the degree of hydrophilicity or hydrophobicity. For "RXD SLA HF" and "RXD SLActive", three sample discs were analysed.

The contact angles were determined using a sessile drop test with ultrapure water (EasyDrop DSA20E, Krüss GmbH). A droplet size of 0.3 µl (microliter) was chosen for the RXD SLA HF samples (i.e. the samples stored dry) and 0.1 µl (microliter) for the RXD SLActive samples (i.e. the samples stored in saline solution). The RXD SLActive samples were blown dry in a stream of Ar prior to the contact angle measurements. The RXD SLA HF samples were measured as received. Contact angles were calculated by fitting a circular segment function to the contour of the droplet on the surface.

The results of the contact angle measurements are given in Table 1a.

TABLE 1a

Contact angles (first set of results)

|  | disc 1 CA [°] | disc 2 CA [°] | disc 3 CA [°] | mean CA [°] | Std CA [°] |
|---|---|---|---|---|---|
| RXD SLA HF | 134.3 | 139.6 | 134.6 | 136.2 | 3.0 |
| RXD SLActive | 0 | 0 | 0 | 0 |  |

As shown in Table 1a, all RXD SLA HF discs were hydrophobic exhibiting a contact angle of about 135° when contacted with pure water, whereas the RXD SLActive discs were hydrophilic showing complete wetting with water.

In further experiments, also RXD SLActive HF samples were assessed for their contact angles, the results of which are shown in Table 1b.

TABLE 1b

Contact angles (second set of results)

|  | disc 1 CA [°] | disc 2 CA [°] | disc 3 CA [°] | mean CA [°] | Std CA [°] |
|---|---|---|---|---|---|
| RXD SLA HF | 140.7 | 138.2 | 135.8 | 138.2 | 2.5 |
| RXD SLActive | 0.0 | 0.0 | 0.0 | 0.0 |  |
| RXD SLActive HF | 0.0 | 0.0 | 0.0 | 0.0 |  |

These results confirm the previous findings regarding RXD SLA HF and RXD SLActive samples, and further show complete wetting of the RXD SLActive HF samples, the surface of which can therefore be regarded as superhydrophilic within the above mentioned definition, as it is also the case for the surface of the RXD SLActive samples. Thus, the sub-microscopic structures according to the present invention did not have any negative impact on the hydrophilicity of the surface on which they are formed.

1.2.2. SEM (Scanning Electron Microscopy)

The visual appearance and morphology of the nanostructures were evaluated using scanning electron microscopy (SEM).

SEM measurements were performed on three discs for each type of surface. The measurements were performed on a scanning electron microscope of the type Zeiss Supra 55. The overview SEM images were acquired with an acceleration voltage of 20 kV using the Everhart-Thornley detector and the high-resolution images with an acceleration voltage of 5 kV using the in-lens detector.

The SEM images of the samples are given in the attached figures, whereby

Figure 2:
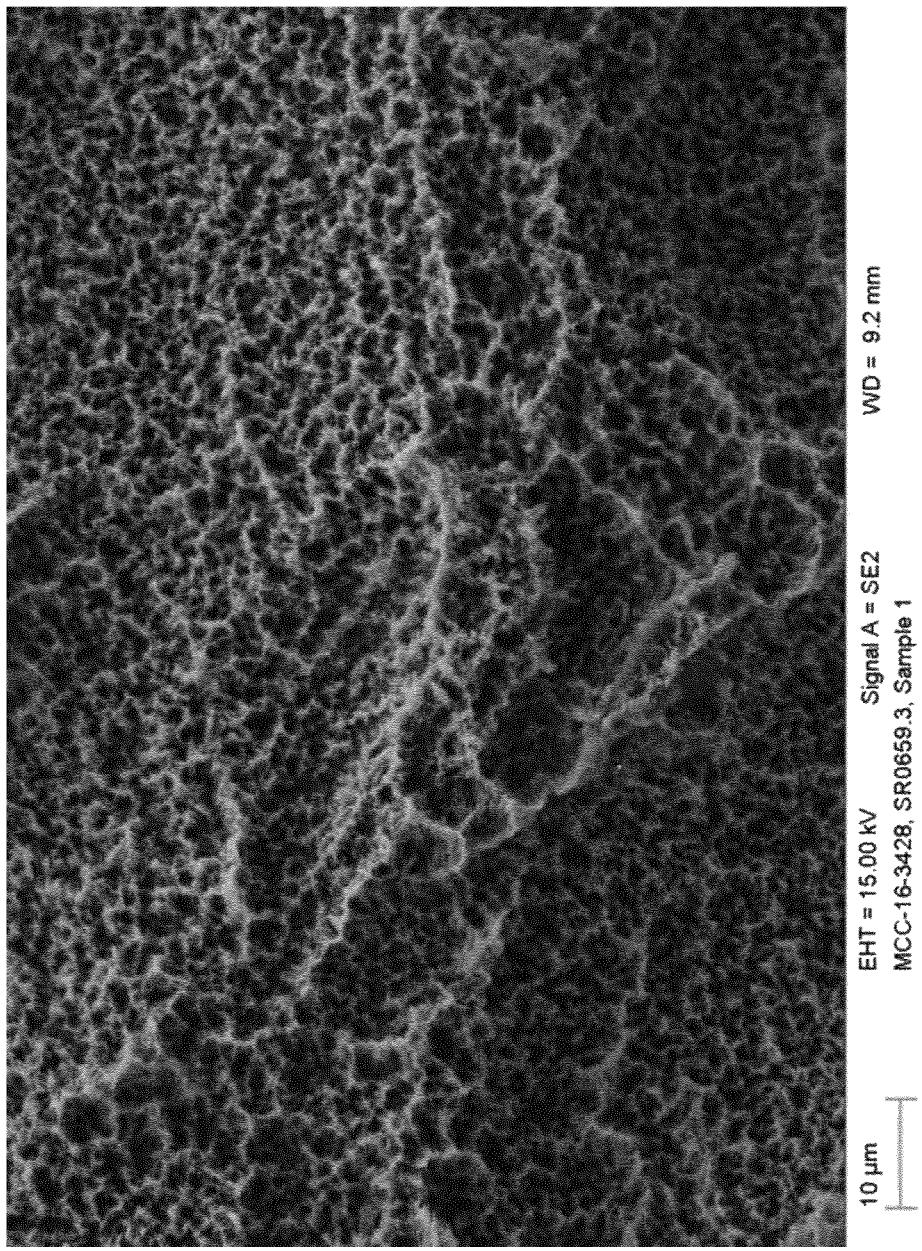
FIG. 2 shows a SEM image of the surface of sample RXD SLActive HF in a magnification of about 1,000×.
Figure 3:
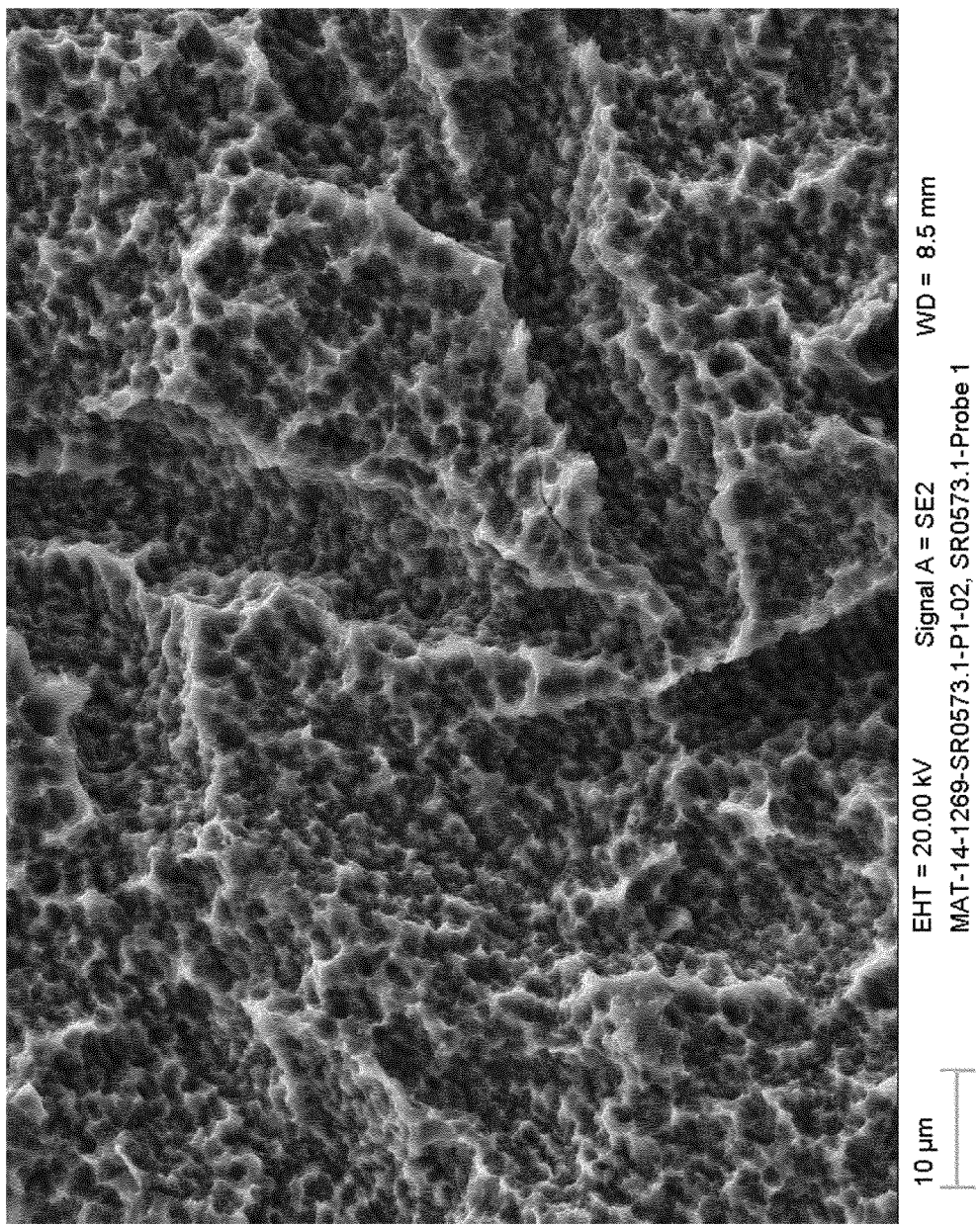
FIG. 3 shows a SEM image of the surface of sample RXD SLActive in a magnification of about 1,000×.
Figure 4:
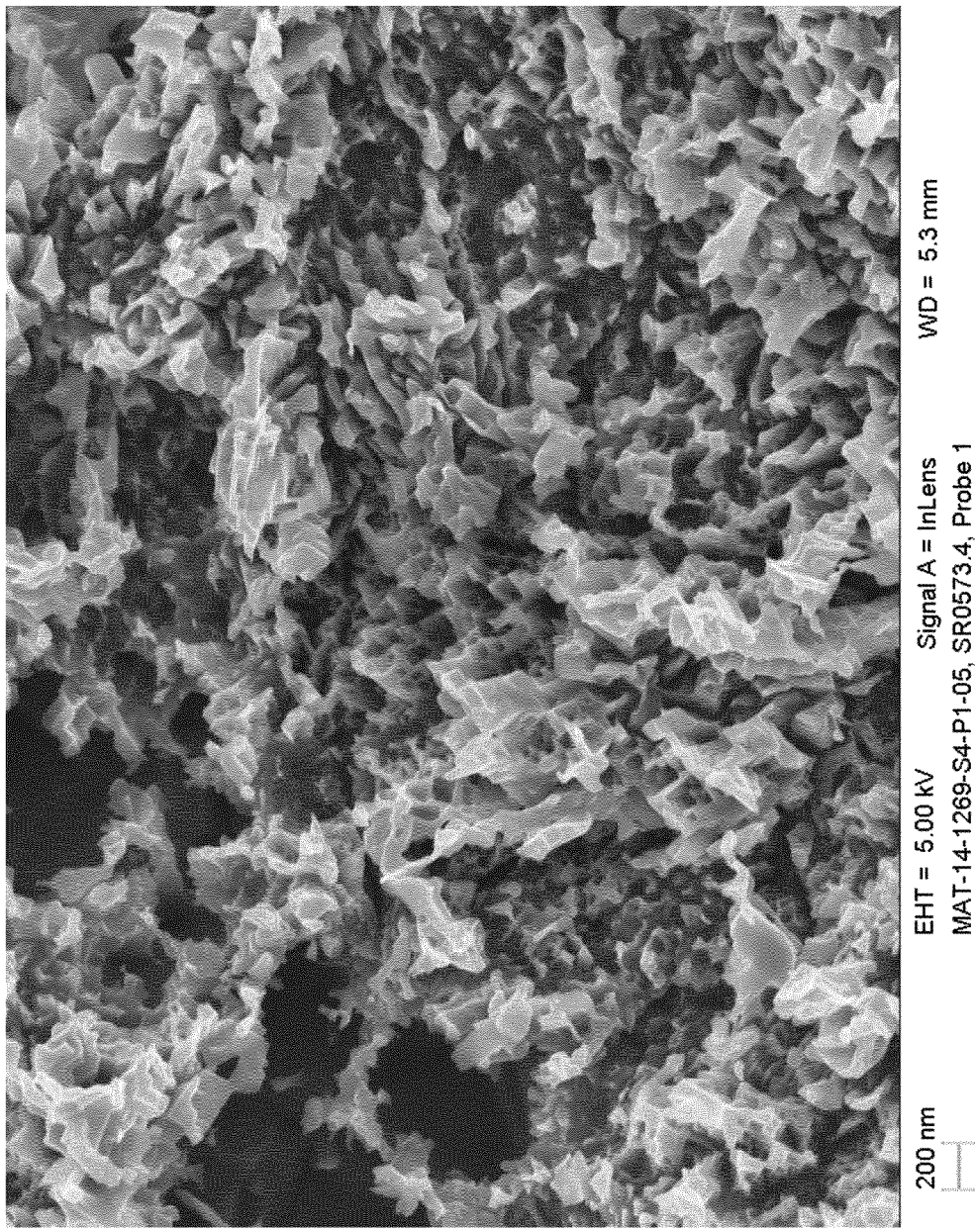
FIG. 4 shows a SEM image of the surface of sample RXD SLA HF in a magnification of about 20,000×.
Figure 5:
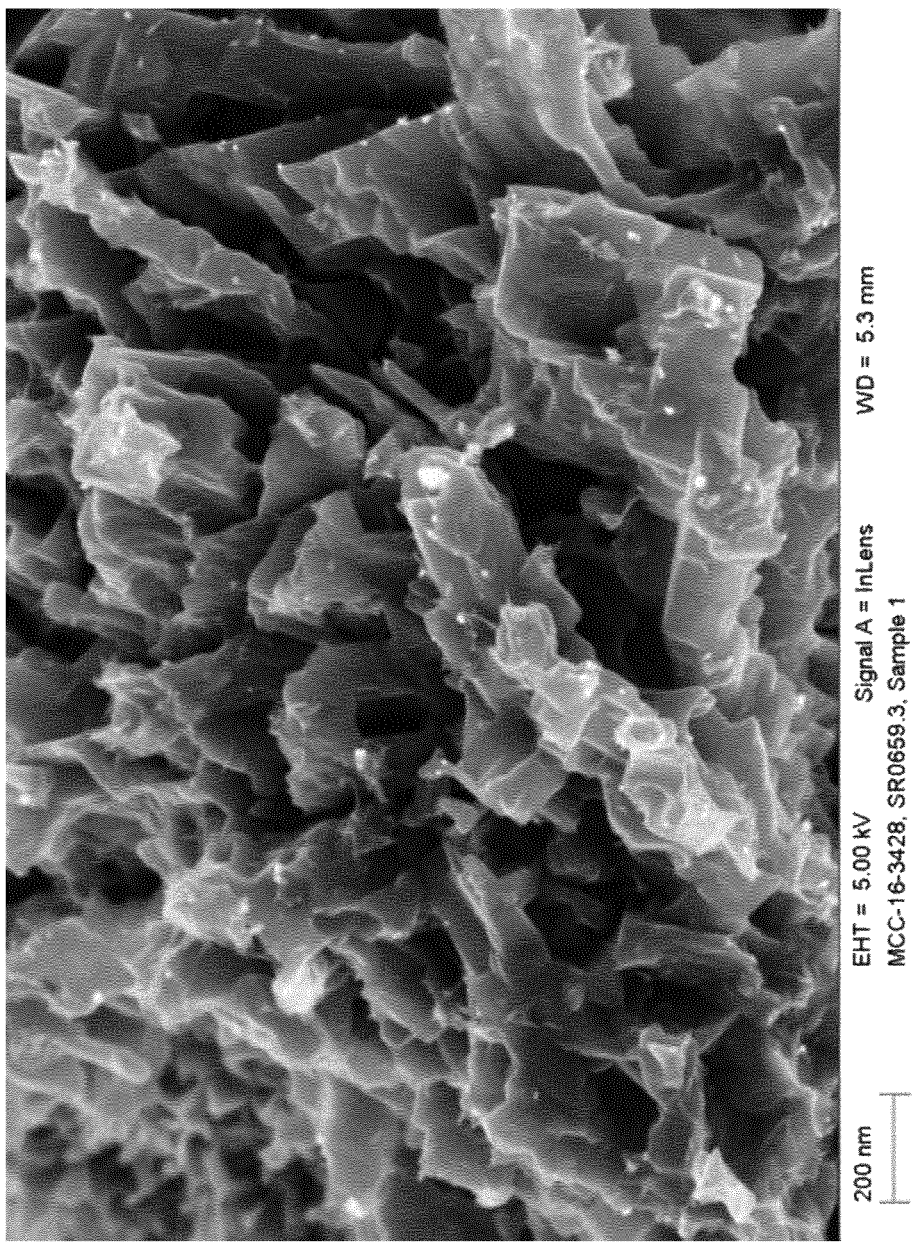
FIG. 5 shows a SEM image of the surface of sample RXD SLActive HF in a magnification of about 50,000×.
Figure 6:
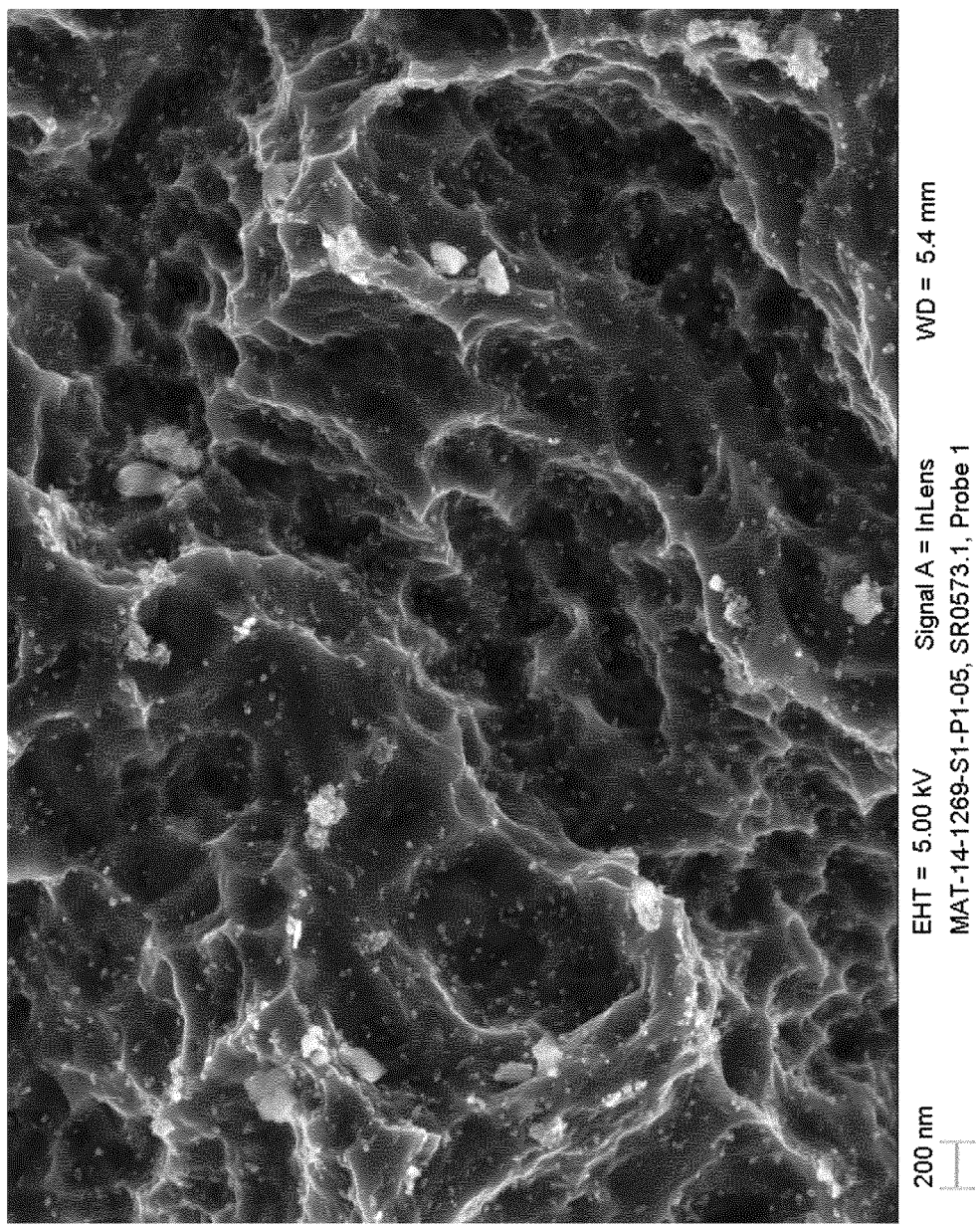
FIG. 6 shows a SEM image of the surface of sample RXD SLActive in a magnification of about 20,000×.

FIG. 1 relates to a SEM image of the surface of sample RXD SLA HF in a magnification of about 1,000×, the scale corresponding to 10 micrometer being given in the bottom left corner of the image;

FIG. 2 relates to a SEM image of the surface of sample RXD SLActive HF in a magnification of about 1,000×, the scale corresponding to 10 micrometer being given in the bottom left corner of the image;

FIG. 3 relates to a SEM image of the surface of sample RXD SLActive in a magnification of about 1,000×, the scale corresponding to 10 micrometer being given in the bottom left corner of the image;

FIG. 4 relates to a SEM image of the surface of sample RXD SLA HF in a magnification of about 20,000×, the scale corresponding to 200 nanometer being given in the bottom left corner of the image;

FIG. 5 relates to a SEM image of the surface of sample RXD SLActive HF in a magnification of about 50,000×, the scale corresponding to 200 nanometer being given in the bottom left corner of the image; and FIG. 6 relates to a SEM image of the surface of sample RXD SLActive in a magnification of about 20,000×, the scale corresponding to 200 nanometer being given in the bottom left corner of the image.

As can be seen from FIGS. 1 to 6, the samples exhibit the macroscopic and microscopic topographical formation obtained by the SLA® treatment, namely by sandblasting and etching the samples in a boiling mixture of HCl and $H_2SO_4$.

However, there are distinct differences in the appearance of a sub-microscopic topographical formation. Specifically, sub-microscopic structures are formed by subtractive process step b), i.e. by the etching using an etching solution comprising HF.

The sub-microscopic structures have a shape with at least one straight-line edge, and more particularly are sharp-edged or even jagged, as can in particular be seen from FIG. 4. Further experiments have shown that the sub-microscopic topographical formation is maintained after storing the RXD SLA HF samples in NaCl or in air.

Also, similar structures were obtained if an SLA® or an SLActive® surface was taken as a starting point, as shown by FIGS. 4 and 5 (which were taken at different magnification).

The sub-microscopic structures formed by the process of the present invention including subtractive process step b) are both in size and shape completely different from the nanostructures on the RXD SLActive samples, which are formed according to the technology described in WO2013/056844 and thus are formed by a gradual "growing" or "building up" over time.

1.2.3. Roughness Parameter Determination

Roughness images were acquired using a confocal microscope (psurf explorer, NanoFocus AG, Oberhausen, Germany) equipped with a 20× lens. Three measurements were performed on each sample disc and three discs were measured for each type of surface. The roughness parameters were calculated using the WinSAM software mentioned above. The whole roughness image with a size of 798 μm (micrometer)×798 μm (micrometer) was used for the calculation of the 3D roughness parameters.

The values of the microscopic topographical formation (roughness) were determined using a moving average Gaussian filter with a cut-off wavelength of 30 μm (x=31 μm, y=30 μm, 20×19 image points). Then, the roughness values were calculated by means of a KFL analysis with limits from the amplitude density.

Specifically, $S_a$ (the arithmetic mean deviation of the surface in three dimensions), $S_t$ (the maximum peak to valley height of the profile in three dimensions) and $S_{sk}$ (the skewness) were determined in analogy to EN ISO 4287 relating to the respective parameters $R_a$, $R_t$ and $R_{sk}$ in two dimensions. For the parameters in three dimensions, it is further referred to ISO 25178, in which the symbol $S_z$ is used for the maximum peak to valley height of the profile (instead of the symbol $S_t$ used in the context of the present invention).

Table 2a presents the mean values of the microroughness values of the two samples. The table shows that at least the values of $S_a$ and $S_t$ of both RXD SLActive and RXD SLA HF lie within the same range typically observed for SLA®/SLActive® implants. Specifically, the $S_a$ and $S_t$ values of RXD SLA HF deviate from the respective values of the RXD SLActive samples by less than 15%.

TABLE 2a

Values of the microscopic topographical formation (first set of results)

| | Sa [μm] | Std Sa [μm] | St [μm] | Std St [μm] | Ssk | Std Ssk |
|---|---|---|---|---|---|---|
| RXD SLA HF | 1.080 | 0.024 | 6.81 | 0.13 | 0.261 | 0.037 |
| RXD SLActive | 0.970 | 0.046 | 6.38 | 0.26 | 0.192 | 0.051 |

In further experiments, also RXD SLActive HF samples were assessed for the microscopic topographical formation formed thereon, the results of which (apart from the ones for RXD SLA HF and RXD SLActive) are shown in Table 2b.

TABLE 2b

Values of the microscopic topographical formation (second set of results)

| | Sa [μm] | Std Sa [μm] | St [μm] | Std St [μm] | Ssk | Std Ssk |
|---|---|---|---|---|---|---|
| RXD SLA HF | 1.065 | 0.046 | 7.56 | 0.42 | 0.270 | 0.035 |
| RXD SLActive | 1.068 | 0.020 | 7.00 | 0.16 | 0.181 | 0.047 |
| RXD SLActive HF | 1.048 | 0.029 | 7.40 | 0.14 | 0.286 | 0.026 |

These results confirm the previous findings regarding RXD SLA HF and RXD SLActive samples and further show only a slight deviation of the topography parameters determined for RXD SLActive HF samples in comparison to the ones determined for RXD SLActive. Specifically, a deviation of the $S_a$ and $S_t$ values of less than 15% was found for the RXD SLActive HF samples in comparison to the RXD SLActive samples.

1.2.4. Protein Adsorption Measurements

Albumin (from bovine serum (BSA), Alexa Fluor 647 conjugate, Invitrogen, USA), fibrinogen (from human plasma; HPF, Alexa Fluor 546 conjugate, Invitrogen, USA) and fibronectin (Rhodamine Fibronectin from bovine plasma; BSF, Cytoskeleton, Inc., USA) were used as model proteins to study their adsorption (or "adherence") behaviour on the different surfaces by means of fluorescence microscopy using a fluorescence scanner.

Stock solutions of 0.5 mg/ml albumin and 0.5 mg/ml fibrinogen have been made according to the product manuals. For storage these stock solutions were divided into 0.5 ml aliquots and frozen at −20° C. Fibronectin solutions were made directly from the 20 μg vials, without making a stock solution.

All protein-adsorption solutions were made with HEPES 2 buffer prepared with 10 mM 4-(2-hydroxylethyl)-piperazine-1-ethanesulfonic acid (HEPES) and 150 mM NaCl with pH 7.4. Prior to use the HEPES 2 buffer was filtered (Whatman FP 30/0.2 CA-S, size 0.2 μm, maximum pressure 7 bar).

For low protein concentration experiments, the protein solution consisted of filtered HEPES 2 and fluorescently labelled protein of defined concentration (see Table 3 below). For high concentration experiments, unlabelled protein was added additionally to simulate the real protein concentration in human blood (Table 3). To enhance the solubility of unlabelled proteins, HEPES 2 was heated to 37° C. (water bath, INCO 2/108, Memmert GmbH&Co, Germany) prior to the preparation of the solution. The different proteins were tested separately; therefore, the prepared protein solutions always contained only one type of protein. It is assumed that the labelled proteins behave like the unlabelled ones.

To reduce a possible uncertainty in the results due to the instability of the fluorescence marker, the protein solution was freshly prepared right before the adsorption experiments.

The method applied was based on the application of fluorescently labelled proteins and intensity measurements as well as comparison of fluorescence scanning images.

For the albumin and fibrinogen experiments, the samples were generally immersed into 2 ml of protein solution for 10 minutes. The adsorption process was carried out in 24-well plates. Experiments with fibronectin were carried out in 96-well plates and 0.3 ml protein solution but also with an adsorption time of 10 minutes. All adsorption experiments were performed at room temperature.

Proteins not adsorbed onto the surface were removed by submerging the samples in 2 ml of pure HEPES 2 for 10 seconds. Next, they were pivoted in 5 ml of HEPES 2 for 5 seconds followed by a rinsing step with the same 5 ml of HEPES 2. Additionally, the samples were rinsed with ultra-pure water for 3 seconds, dried in a stream of nitrogen (at a pressure of about 1 bar) and stored at room temperature in a 24-well plate. To avoid bleaching of the fluorescent label of the adsorbed proteins, the well plates were covered with aluminium foil.

The experimental conditions are given in Table 3 below:

TABLE 3

Experimental conditions of protein adsorption experiments

| Protein | Concentration | Protein solution | Time | Samples |
|---|---|---|---|---|
| low protein concentration | | | | |
| Albumin | 3 µg/mL | 2 mL | 10 min | 6 |
| Fibrinogen | 7 µg/mL | 2 mL | 10 min | 6 |
| Fibronectin | 3 µg/mL | 0.3 mL | 10 min | 6 |
| high protein concentration | | | | |
| Albumin | 3 µg/mL + 10 mg/mL* | 2 mL | 10 min | 6 |
| Fibrinogen | 7 µg/mL + 1 mg/mL* | 2 mL | 10 min | 6 |
| Fibronectin | 3 µg/mL + 0.2 mg/mL* | 0.3 mL | 10 min | 6 |

*= unlabelled protein

The amount of protein attached to the surface was measured qualitatively using a microarray fluorescence scanner (Axon Genepix 4200A, Molecular Devices, USA). For intensity measurements, the resolution was set to 100 µm/pixel and only one scan per line was performed. For imaging the resolution was set to 5 µm/pixel and three scans per line were performed. To read out the albumin adsorption a laser with a wavelength of 635 nm was used whereas the scanning of fibrinogen and fibronectin adsorbed surfaces was performed using a 532 nm laser. The best focus position was determined separately for every sample.

The photo-multiplier tube (PMT) of the fluorescence scanner was specified to be linear between a gain of 350 to 600. For that reason, all scans were performed in this PMT range. The gain was adapted for each combination of surface, protein and concentration in order to stay in the grey-scale limits of the fluorescence signal of a sample. All gains chosen are listed in Table 4.

TABLE 4

Gains chosen for every batch of samples to measure the protein adsorption

| | RXD SLActive | RXD SLA HF |
|---|---|---|
| low protein concentration | | |
| Albumin | 400 | 600 |
| Fibrinogen | 450 | 650 |
| Fibronectin | 500 | 600 |
| high protein concentration | | |
| Albumin | 600 | 600 |
| Fibrinogen | 550 | 550 |
| Fibronectin | 550 | 600 |

To evaluate the homogeneity of the protein adsorption, high-resolution images were compared with each other by visual examination.

Figure 7:
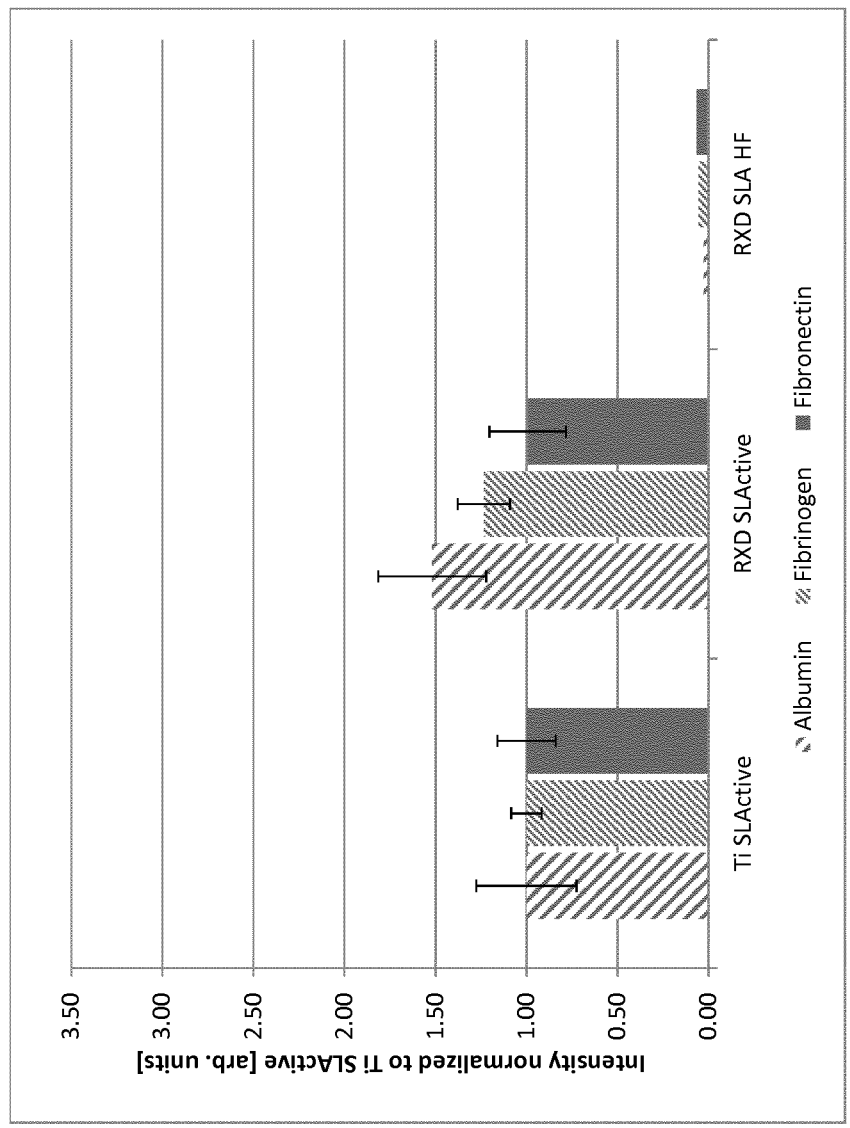
FIG. 7 shows a diagram relating to the fluorescence intensities measured for albumin, fibrinogen and fibronectin on RXD SLA HF surfaces at a low protein concentration.
Figure 8:
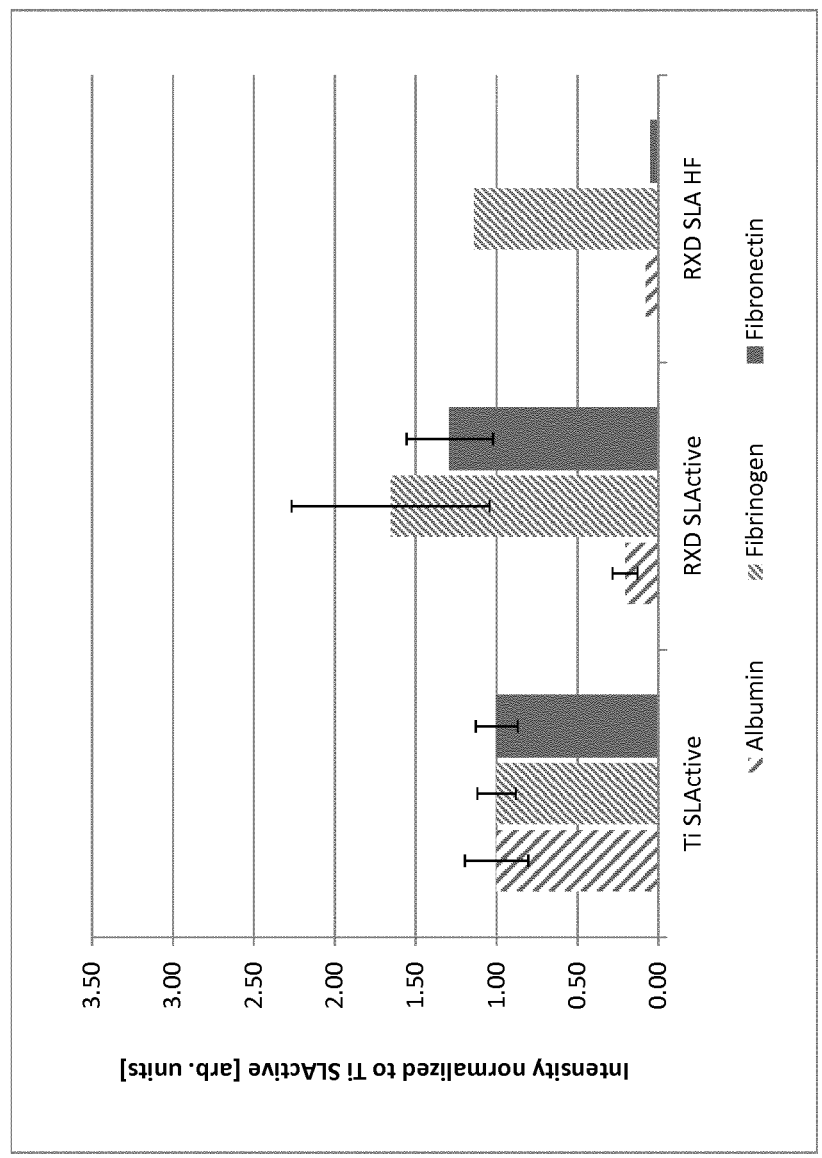
FIG. 8 shows a diagram relating to the fluorescence intensities measured for albumin, fibrinogen and fibronectin on RXD SLA HF surfaces at a high protein concentration.

The fluorescence intensity data acquired by fluorescence scanning are given in the attached FIG. 7 showing a diagram relating to the fluorescence intensities measured for albumin, fibrinogen and fibronectin on RXD SLA HF surfaces at the low protein concentration defined above; and FIG. 8 showing a diagram relating to the fluorescence intensities measured for albumin, fibrinogen and fibronectin on RXD SLA HF surfaces at the high protein concentration defined above.

All values presented in FIGS. 7 and 8 are normalized to the respective intensities measured for a titanium body treated according to the SLActive® protocol (Ti SLActive). The error bars indicate the standard deviation.

According to FIG. 7, a much lower adsorption of all proteins was determined for the hydrophobic RXD SLA HF surface, than for the hydrophilic Ti SLActive and RXD SLActive surface at low protein concentration.

At high protein concentration, a very selective adsorption of fibrinogen was determined for the RXD SLA HF according to the present invention with an intensity comparable to the one of fibrinogen adsorbed on well-established Ti SLActive, as shown in FIG. 8. At both low protein concentration and high protein concentration, non-specific adsorption of albumin was much lower for RXD SLA HF than for comparative Ti SLActive and for RXD SLActive.

1.2.5. Assessment of Fibrin Network Formation after Whole Human Blood Incubation RXD SLActive HF samples were incubated with whole human blood and analysed for fibrin network formation by SEM and CLSM (confocal laser scanning microscopy) imaging.

Specifically, whole human blood obtained from healthy volunteers was partially heparinized directly with 3 IU/ml sodium heparin (final concentration 0.5 IU heparin/ml blood) and used for the experiments within 1 hour after withdrawal.

Samples were placed into a sample holder and freshly withdrawn blood was added until all samples were covered with a 4 mm thick layer of blood. To prevent further contact with air, the sample holder was closed with a lid and sealed with parafilm before incubation on a tumbling shaker at 10 rpm at room temperature.

The incubation time was determined for each experiment individually. For this, whole blood was spiked with labeled fibrinogen (Alexa488), which allows live monitoring of the blood coagulation on the samples using the fluorescence microscope. As reference, the samples RXD SLActive (and RXD SLA) were used and two time points were chosen (t1: thin, t2: thick fibrin network present on the reference sample).

After incubation, blood was removed and the samples were washed three times by adding pre-warmed PBS into the sample holder, then incubated on a tumbling shaker at 10 rpm for 1 minute for each washing step. Thereafter, the samples were transferred into a new 96-well plate for further treatment.

For SEM imaging, samples were fixed in modified Karnovsky solution for 1 h at room temperature (RT) and then washed twice in PBS. Thereafter the samples were dehydrated by immersing the samples in solutions of a gradient series of ethanol (50, 70, 80, 90 and 100%), followed by incubation in hexamethyldisilazane (HMDS) for 30 min. Finally, samples were placed into a new 96-well plate and dried overnight at RT. On the next day samples were sputter-coated with gold/palladium (high vacuum coater Leica EM ACE 600, Switzerland). SEM imaging was performed using a Hitachi S-4800 (Hitachi High-Technologies, Canada) at an accelerating voltage of 2 kV and 10 µA current flows.

For CLSM analysis, samples were incubated for 30 min in PBS with 5% goat serum and 1% FCS before staining platelets with Alexa546-labeled phalloidin for 1 h at RT. The platelets and the fibrin network (visible due to spiking of the blood with Alexa488-labeled fibrinogen) were imaged with the CLSM (10×, 40× magnification). Depending on the coverage and thickness of the fibrin network seen by SEM imaging, only one time point (t1 or t2) was imaged. On samples showing complete coverage with fibrin on the surface, the thickness of the fibrin network was measured from z-stack images. To assess the thickness of the fibrin network, 4 z-stack images of 2 samples (2 images per sample with 4 to 6 measurements per image) were analysed to measure the distance from the sample surface to the top surface of the fibrin network using the measure function of the Zeiss ZEN software. CLSM analysis was performed with three independent experiments.

The semi-quantitative analysis of the SEM imaging revealed a trend for higher fibrin network thickness and larger sample coverage of the RXD SLActive HF sample in comparison to the RXD SLActive sample.

This is evidenced by the following figures, of which

Figure 9:
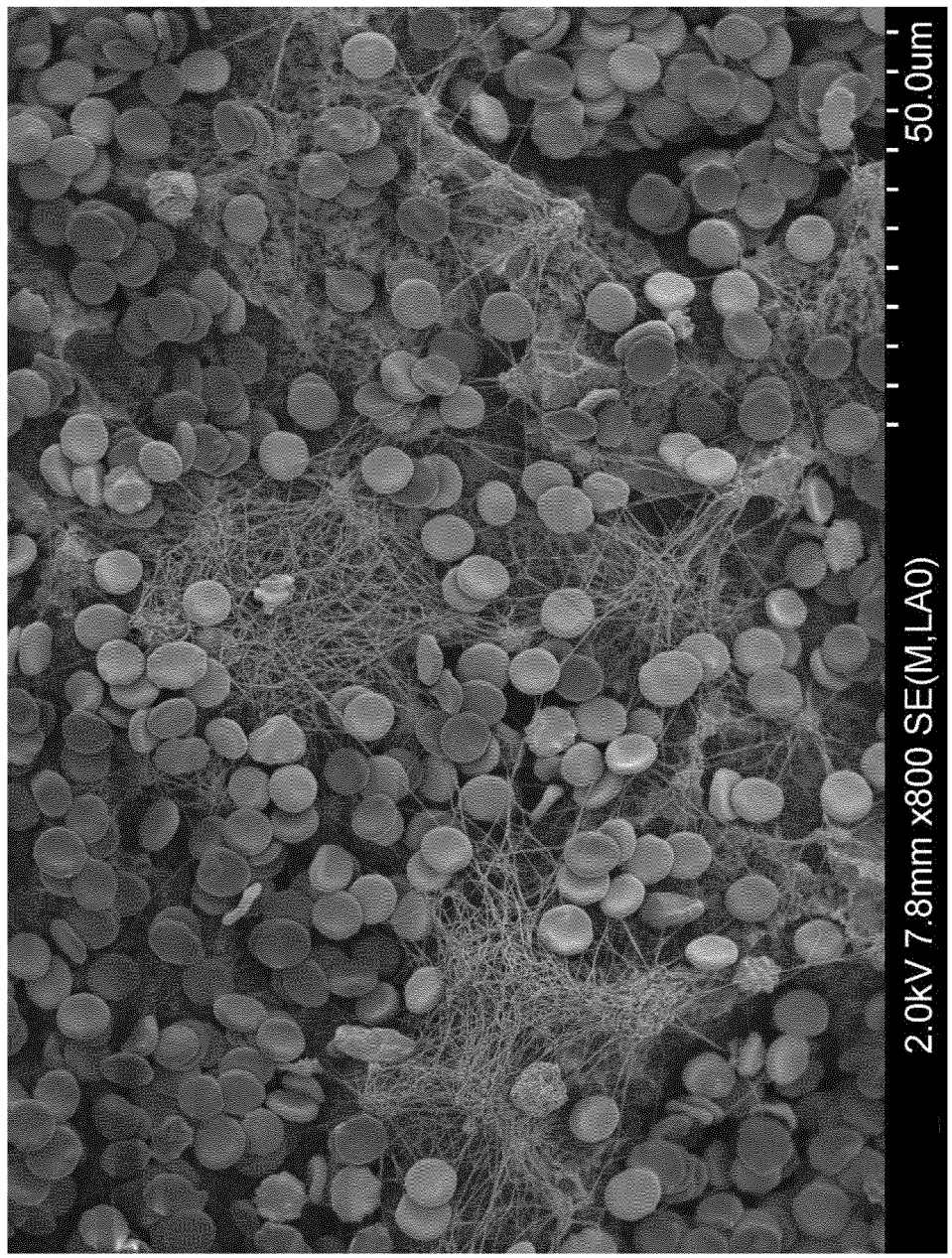
FIG. 9 shows a SEM image of the surface of sample RXD SLActive HF after 14 minutes of incubation in magnification of about 800×.
Figure 10:
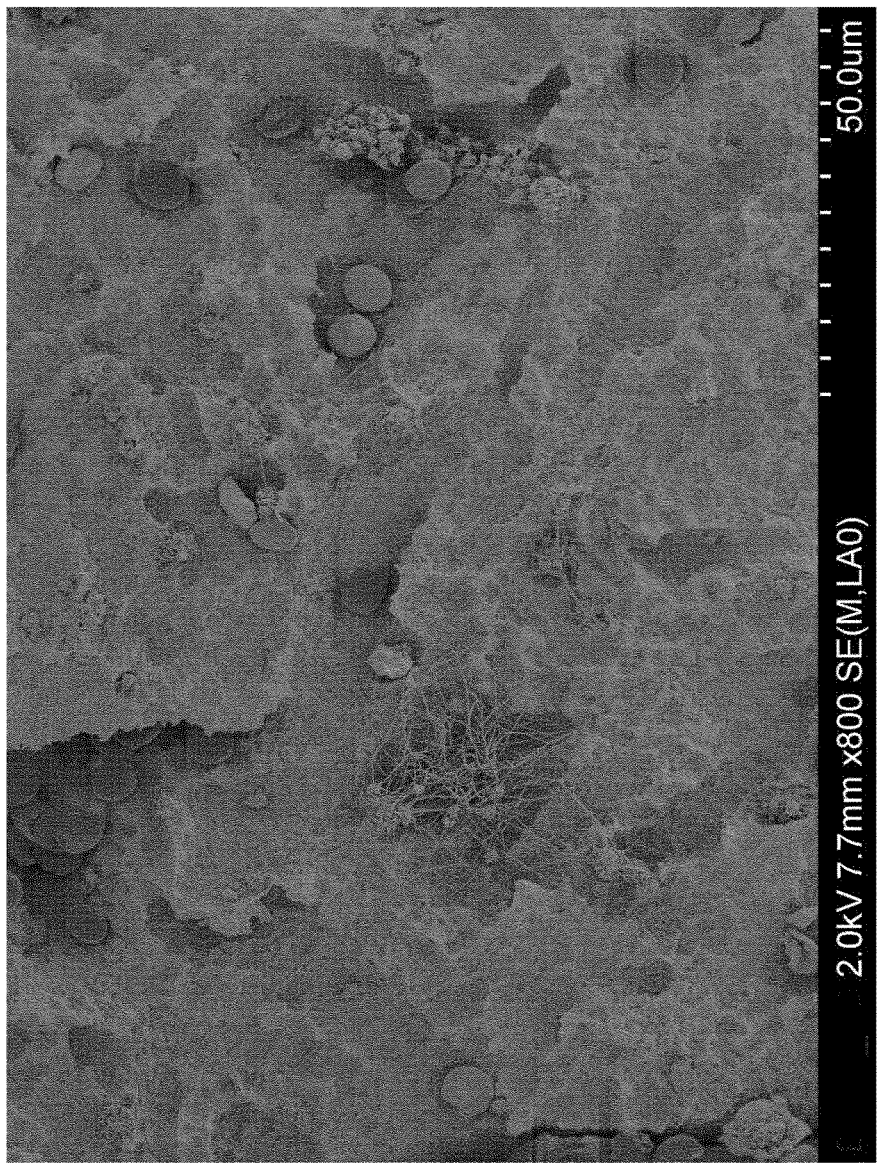
FIG. 10 shows a SEM image of the surface of sample RXD SLActive after 14 minutes of incubation in magnification of about 800×.

FIG. 9 relates to a SEM image of the surface of sample RXD SLActive HF after 14 minutes of incubation in a magnification of about 800×, the scale corresponding to 50 micrometer being given in the bottom right corner of the image; and FIG. 10 relates to a SEM image of the surface of sample RXD SLActive after 14 minutes of incubation in a magnification of about 800×, the scale corresponding to 50 micrometer being given in the bottom right corner of the image.

Evaluating the presence, distribution and thickness of the fibrin network, the semi-quantitative analysis of the SEM images is summarized in Table 5 showing for four different experiments the value of a qualitative ranking from 0 to 4 taken in each case for two samples and for two different incubation periods given in the table, the ranking starting from patches of blood cells with only few visible fibrin fibers (0) to thick fibrin networks completely covering the sample surface (4).

TABLE 5

Semi-quantitative analysis of the SEM images for four different experiments performed on RXD SLActive HF and RXD SLActive samples

| Experiment | Incubation period (min) | RXD SLActive HF | | RXD SLActive | |
| --- | --- | --- | --- | --- | --- |
| 1 | 10 | 1 | 2 | 1.5 | 1.5 |
|   | 15 | 2 | 4 | 2 | 4 |
| 2 | 12 | 1.5 | 1.5 | 1 | n.d. |
|   | 15 | 3.5 | 2 | 0.5 | 1 |
| 3 | 14 | 3 | 3 | 0.5 | 1 |
|   | 17 | 4 | 2.5 | 4 | 2 |
| 4 | 15 | 4 | 4 | 4 | 4 |
|   | 18 | 4 | 4 | 2 | 1.5 |

The thickness of fibrin formed on samples incubated with whole blood (partially heparinized 0.5 IU/ml) for 15 minutes and 17 minutes, respectively, has been assessed as described above, the results of which are given in Table 6.

TABLE 6

Analysis of fibrin layer thickness of RXD SLActive HF and RXD SLActive samples

| | 15 minutes incubation | | 17 minutes incubation | |
| --- | --- | --- | --- | --- |
| Sample | fibrin layer | thickness [µm] | fibrin layer | thickness [µm] |
| RXD SLActive HF | homogenous | 16.93 | homogenous/ spots | 14.29 |
| RXD SLActive | homogenous | 13.97 | homogenous | 9.86 |

Thus, higher fibrin thickness was determined on the samples according to the present invention than on the comparative samples.

2. Examples Relating to In Vivo-Analysis

Biomechanical studies in rabbits were performed to investigate the influence of the surface topography on the osseointegration. The attachment between bone and implant was directly assessed by pull-out tests.

2.1. Materials and Methods

Additionally, biomechanical studies in rabbits were performed to investigate the osseointegration of titanium implant discs in vivo. For these additional studies, discs were prepared as described for the in-vitro experiments, but using Roxolid discs with 6.2 mm in diameter and 2 mm in thickness. The respective samples are in the following referred to as "RXD SLA HF II".

2.2. Characterization of the Surface of the Samples

The samples were analysed using the above described procedures for contact angle measurement and roughness parameter determination.

Regarding contact angle measurement, a mean value of 123.2° was measured for "RXD SLA HF II".

Roughness parameter determination produced the results given in Table 7.

TABLE 7

Roughness values of the microscopic topographical formation of the RXD SLA HF II samples of the in vivo study

| | $S_a$ [µm] | Std $S_a$ [µm] | $S_t$ [µm] | Std $S_t$ [µm] | Ssk | Std Ssk |
| --- | --- | --- | --- | --- | --- | --- |
| RXD SLA HF II | 1.204 | 0.069 | 8.17 | 0.42 | 0.306 | 0.031 |

The results given in Table 7 confirm the findings obtained above, namely that at least the values of $S_a$ and $S_t$ of RXD SLA HF II lie within the same range typically observed for SLA®/SLActive® implants. Also, with regard to the samples of the in vivo study, the $S_a$, $S_t$ and $S_{sk}$ are only unsubstantially changed by process step b), i.e. the formation of the sub-microscopic topographical formation.

2.3. Biomechanical Pull-Out Measurements

As mentioned above, pull-out studies were performed in rabbits. To this end, rabbits were sedated and, during standard surgical procedures, received two disc-implants per tibia, i.e. four implants in total per rabbit.

The implants were provided with a Teflon cap to protect them from bone overgrowth and were stabilized with a pre-shaped titanium band, retained in the cortical bone with two titanium screws. After the implant procedures, the soft tissue layers were repositioned and the wound closed using a resorbable suture.

Bone-implant attachments were tested 4 weeks after implantation.

Detailed information concerning the surgery procedure as well as the pull-out test description has already been published elsewhere by Remold and Ellingsen (Biomaterials 23 (2002) 2201) and Monjo et al. (Monjo et al., Biomaterials 29 (2008) 3771).

Table 8 gives the measured pull-out-force in [N] after 4 weeks of implantation.

TABLE 8

| Pull-out-force after 4 weeks of implantation | | | |
|---|---|---|---|
| | Mean Pull-Out-Force [N] | Std | Median |
| RXD SLA HF II | 50.3 | 23.32 | 50.9 |

As can be clearly seen from the Table 8, a very high pull-out-force was determined for RXD SLA HF prepared according to the present invention. Given the relatively high hydrophobicity of the surface of RXD SLA HF, this result is most surprising and emphasizes the relevance of the sub-microscopic topographical formation achieved in subtractive process step b) of the present invention.

The invention claimed is:

1. A process for preparing a topography for improved blood coagulation and/or cell attachment on a body made of titanium or a titanium alloy, the process comprising:
   a) etching at least a portion of a surface of the body with a first etching solution comprising a mineral acid to form a microscopic topographical formation, and
   b) then etching the surface etched under a) with a second etching solution different than the first etching solution to form a sub-microscopic topographical formation in the microscopic topographical formation, said second etching solution comprising hydrofluoric acid,
   wherein if hydrofluoric acid is contained in the first etching solution, a concentration of the hydrofluoric acid in the first etching solution is lower than a concentration of hydrofluoric acid in the second etching solution.

2. The process according to claim 1, wherein by the sub-microscopic topographical formation formed in step b), at least one surface parameter defining the microscopic topographical formation formed in step a) is changed by 50% at most, the at least one surface parameter being selected from the group consisting of: arithmetic mean deviation of the surface in three dimensions (Sa), a maximum peak to valley height of a profile in three dimensions (St), and a skewness of the profile in three dimensions (Ssk).

3. The process according to claim 1, wherein the sub-microscopic topographical formation comprises or essentially consists of sub-microscopic structures which extend in at least two dimensions to 1000 nm at most.

4. The process according to claim 1, further comprising providing a macroscopic topographical formation to the surface prior to step a).

5. The process according to claim 1, wherein the body is made of a titanium-zirconium alloy.

6. The process according to claim 1, wherein the concentration of hydrofluoric acid in the second etching solution is in a range from 0.01 vol.-% to 4 vol.-%.

7. The process according to claim 1, wherein the etching under step b) is carried out for a duration in a range of from 0.1 minute to 30 minutes.

8. The process according to claim 1, wherein the etching under step b) is carried out at a temperature in a range of from 10° C. to 90° C.

9. The process according to claim 1, wherein the first etching solution comprises or essentially consists of a mixture of HCl and $H_2SO_4$.

10. The process according to claim 1, wherein the body is a dental implant or a dental implant abutment and the topography is provided on at least a portion of the surface of the body that in use is intended to be in contact with bone tissue or soft tissue, respectively.

11. The process according to claim 1, wherein the etching in step b) is a subtractive process in which the second etching solution dissolves and removes material from the surface of the body to alter the topography of the body.

12. The process according to claim 1, wherein the microscopic topographical formation is defined by at least one surface parameter selected from the group consisting of:
   i) an arithmetic mean deviation of the surface in three dimensions (Sa) in a range of from 0.1 µm to 2.0 µm;
   ii) a maximum peak to valley height of a profile in three dimensions (St) in a range of from 1.0 µm to 20.0 µm; and
   iii) a skewness of the profile in three dimensions (Ssk) in a range of from −0.6 to 1.0.

13. The process according to claim 1, wherein the first etching solution is devoid of hydrofluoric acid.

14. The process according to claim 1, wherein the etching in steps a) and b) are subtractive processes in which the first etching solution and the second etching solution respectively dissolve and remove material from the surface of the body to alter the topography of the body, the material being dissolved and removed being more than a native oxide layer of the body.

* * * * *